United States Patent [19]

Kelly

[11] Patent Number: 5,110,986
[45] Date of Patent: May 5, 1992

[54] SYNTHESIS OF N-T-ALKYL-1,2-DIACYLHYDRAZINES

[75] Inventor: Martha J. Kelly, Norristown, Pa.

[73] Assignee: Rohm and Haas Company, Philadelphia, Pa.

[21] Appl. No.: 186,328

[22] Filed: Apr. 26, 1988
[51] Int. Cl.$^5$ .............. C07C 241/02; C07D 409/12; C07D 407/12; C07D 405/12
[52] U.S. Cl. .................... 564/149; 544/182; 544/194; 544/204; 544/208; 544/209; 544/210; 544/211; 544/212; 544/213; 544/215; 544/219; 544/224; 544/238; 544/239; 544/240; 544/242; 544/295; 544/296; 544/298; 544/299; 544/300; 544/301; 544/322; 544/324; 544/325; 544/326; 544/327; 544/328; 544/329; 544/330; 544/331; 544/332; 544/333; 544/335; 544/336; 544/357; 544/405; 544/406; 544/407; 546/184; 546/186; 546/189; 546/192; 546/193; 546/195; 546/201; 546/205; 546/206; 546/208; 546/209; 546/212; 546/214; 546/215; 546/216; 546/221; 546/222; 546/224; 546/225; 546/244; 546/245; 548/225; 548/226; 548/227; 548/228; 548/229; 548/230; 548/231; 548/232; 548/233; 548/236; 548/243; 548/244; 548/245; 548/246; 548/247; 548/248; 548/249; 548/251; 548/253; 548/255; 548/262.6; 548/262.8; 548/263.2; 548/263.6; 548/263.8; 548/264.2; 548/264.4; 548/264.8; 548/265.2; 548/265.4; 548/265.6; 548/266.4; 548/266.6; 548/267.4; 548/267.6; 548/455; 548/460; 548/461; 548/465; 548/467; 548/483; 548/484; 548/485; 548/492; 548/493; 548/510; 548/517; 548/518; 548/519; 548/520; 548/522; 548/523; 548/527; 548/530; 548/531; 548/533; 548/534; 548/535; 548/536; 548/537; 549/59; 549/60; 549/61; 549/62; 549/63; 549/64; 549/473; 549/474; 549/475; 549/476; 549/478; 549/479; 549/480; 549/481; 549/484; 549/485; 549/486; 549/487; 558/393; 558/415; 558/416; 558/442; 558/445; 560/20; 560/21; 560/22; 560/24; 560/25; 560/28

[58] Field of Search ............. 564/135, 149, 150, 151, 564/51, 59, 134; 560/158, 20, 21, 22, 24, 25, 28, 29, 30, 34; 549/487, 59, 60, 61, 62, 63, 64, 473, 474, 475, 476, 478, 479, 480, 481, 484, 485, 486; 544/182, 194, 204, 208, 209, 210, 211, 212, 213, 215, 219, 224, 238, 239, 240, 242, 295, 296, 298, 299, 300, 301, 322, 324, 325, 326, 327, 328, 329, 330, 331, 332, 333, 335, 336, 357, 405, 406, 407; 546/184, 186, 189, 192, 193, 195, 201, 205, 206, 208, 209, 212, 214, 215, 216, 221, 222, 224, 225; 548/225, 226, 227, 228, 229, 230, 231, 232, 233, 236, 243, 244, 245, 246, 247, 248, 249, 251, 253, 255, 262.6, 262.8, 263.2, 263.6, 263.8, 264.2, 264.4, 264.8, 265.2, 265.4, 265.6, 266.4, 266.6, 267.4, 267.6, 455, 460, 461, 465, 467, 483, 484, 485, 492, 493, 510, 517, 518, 519, 520, 522, 523, 527, 530, 531, 533; 548/534, 535, 536, 537; 558/393, 415, 416, 442, 445; 562/443, 434, 435, 437, 555, 560

[56] References Cited

U.S. PATENT DOCUMENTS

| | | | |
|---|---|---|---|
| 4,118,358 | 10/1978 | Silver et al. | 260/30.8 R |
| 4,310,696 | 1/1982 | Hojo et al. | 564/464 |
| 4,435,600 | 3/1984 | Hasegawa et al. | 564/464 |

OTHER PUBLICATIONS

Solomons, *Organic Chemistry*, 2nd Ed., John Wiley & Sons, New York, (1980), pp. 191, 192, and 196.
Iwakura et al., "Polyhydrazides. III. N-Methylated Polyhydrazides by Ring-Opening, etc.", *Journal of Polymer Science*: Part A-1, vol. (6), pp. 3381-3393, (1968).
6 *J. Polymer SCI.A*-1, 3381-3393, (1968).

*Primary Examiner*—Glennon H. Hollrah
*Assistant Examiner*—P. O'Sullivan

[57] ABSTRACT

This application relates to a process for preparing a N-t-alkyl-1,2-diacylhydrazine by reacting a 1,3,4-oxadiazole with a tertiary alkyl cation precursor in the presence of a strong acid catalyst. Preferably, the 1,3,4-oxadiazole is a 2,5-disubstituted-1,3,4-oxadiazole and more preferably a 2,5-diaryl-1,3,4-oxadiazole. The strong acid catalyst is preferably a sulfur containing acid and more preferably sulfuric acid.

23 Claims, No Drawings

SYNTHESIS OF N-T-ALKYL-1,2-DIACYLHYDRAZINES

BACKGROUND OF THE INVENTION (1) Field of the Invention

This invention relates to a process for preparing N-t-alkyl-1,2-diacylhydrazines by reacting a 1,3,4-oxadiazole, preferably a 2,5-diaryl-1,3,4-oxadiazole, with a tertiary alkyl cation precursor in the presence of a strong acid catalyst such as sulfuric acid.

The N-t-alkyl-1,2-diacylhydrazines, particularly aromatic, heterocyclic or alkyl substituted N-t-alkyl-1,2-diacylhydrazines, are known to have insecticidal activity against Coleoptera and Lepidoptera. The process of the present invention provides an economic method of producing the desired N-t-alkyl-1,2-diacylhydrazines from inexpensive and readily available starting materials.

(2) Description of the Prior Art

Hasegawa et al U.S. Pat. No. 4,435,600 discloses a process for the preparation of tertiary butyl hydrazine by the direct reaction of t-butanol with a hydrazine salt of a hydrohalogenic acid in the presence of a hydrazine dihydrohalogenide or a hydrogen halide. They considered their reaction to be an improvement over the process of reacting a hydrazine salt of a hydrohalogenic acid with a tertiary butyl halide to obtain a tertiary butyl hydrazine hydrohalogenide and forming the tertiary butyl hydrazine from the tertiary butyl hydrazine hydrohalogenide as disclosed in Hojo et al U.S. Pat. No. 4,310,696.

Iwakura et al, 6 J. Polymer SCI.A-1 3381-3393 (1968), entitled "Polyhydrazides. III. N-Methylated Polyhydrazides by Ring-Opening of Poly-p-phenylene-1,3,4-oxadiazole" discloses a ring-opening methylation reaction of 1,3,4-oxadiazole in fuming sulfuric acid or polyphosphoric acid. At pages 3382 and 3383, they discuss ring-opening reactions of 1,3,4-oxadiazole. In the first reaction 2,5-bis-p-nitrophenyl-1,3,4-oxadiazole was reacted with dimethyl sulfate in oleum. In the second example 1,3,4-oxadiazole was reacted with trimethyl phosphate in polyphosphoric acid.

The Iwakura reaction and the present process proceed by two distinctly different mechanisms. The Iwakura reaction is a second order nucleophilic substitution ($S_N2$). The presently claimed reaction is a first order nucleophilic substitution ($S_N1$).

Further, under the conditions of the Iwakura reaction, the desired N-t-alkyl-1,2-diacylhydrazines are not stable. If the acid anhydride is in excess, as the oleum or polyphosphoric acid in Iwakura, the desired N-t-alkylhydrazine loses the t-alkyl group and cyclizes to the oxadiazole.

SUMMARY OF THE INVENTION

N-t-alkyl-1,2-diacylhydrazines may be prepared by reacting a 1,3,4-oxadiazole with a tertiary alkyl cation precursor in the presence of a strong acid catalyst. Preferably the 1,3,4-oxadiazole is a 2,5-disubstituted-1,3,4-oxadiazole and, more preferably, a 2,5-diaryl-1,3,4-oxadiazole.

The tertiary alkyl cation precursor may be an alcohol, ester, ether, halogen or olefin. The preferred tertiary alkyl cation precursor is an alcohol, acetate, benzoate, methyl ether, ethyl ether, chloride, bromide or olefin. The most preferred precursors are t-butanol, t-butylacetate, t-butylbenzoate, t-butylmethyl ether, t-butylethyl ether and isobutylene.

The strong acid catalyst must be strong enough to open the oxadiazole ring but not so strong as to dehydrate the hydrazine. Acids which include the acid anhydride in excess cause the product hydrazine to revert to the oxadiazole.

The preferred acid catalysts are sulfur containing acids and, more preferably, sulfuric acid. Although hydrogen chloride is a stronger acid than p-toluenesulfonic acid, hydrochloric acid was found not to catalyze the reaction under the conditions tested whereas the p-toluenesulfonic acid was an effective catalyst.

The reaction process is preferably carried out in the presence of a solvent such as a low molecular weight acid, ester, alcohol or ether. "Low molecular weight" is intended to include acids, esters, alcohols and ethers which are liquids at the reaction temperature. The preferred solvents are acetic acid, ethyl acetate, methylbenzoate and diethyl ether. The most preferred solvent is acetic acid.

Depending upon reactants, catalyst and solvent, the process may be carried out between $-20°$ C. and $150°$ C. The process has been carried out between $0°$ C. and $118°$ C. The preferred temperature range is $15°$ C.-$60°$ C. and the most preferred temperature range is $20°$ C.-$30°$ C.

DETAILED DESCRIPTION OF THE INVENTION

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and where indicated higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "haloalkoxy" by itself or as part of another group is an alkoxy group of the stated number of carbon atoms having one or more halo atoms bonded thereto such as difluoromethoxy, trifloromethoxy, 2-fluoroethoxy, 2,2,2-trifluoroethoxy and the like.

"Alkenyl" by itself or as part of another substituent comprises straight and branched chain groups of the stated number of carbon atoms. "Alkenyl" is intended to include alkadienyl, that is, a straight or branched chain alkenyl group comprising two carbon-to-carbon double bonds that can be conjugated such as 1,3-butadienyl, cumulated such as 1,2-propadienyl or isolated such as 1,4-pentadienyl.

The term "tertiary carbon" is meant to refer to a carbon having at least three carbon-to-carbon single bonds.

The term "aryl" should be understood to include those molecules which have a ring structure characteristic of benzene, naphthalene, phenanthrene and anthracene, that is either the six-carbon ring of benzene or the condensed six-carbon rings of other aromatic derivatives. Examples of aryl radicals include unsubstituted and substituted phenyl, benzoyl and naphthalene.

The term "cyclic aromatic radical" should be understood to mean unsaturated cyclic compounds including heterocyclic compounds. Examples of cyclic aromatic radicals include aryl, indolyl, thienyl, furyl, pyrrolyl, triazolyl and tetrazolyl.

Representative examples of six-membered heterocycles having one, two, three or four nitrogen atoms and two to five nuclear carbon atoms include 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 3-pyrazinyl, 2-(1,3,5-triazinyl), 3-(1,2,4-triazinyl), 5-(1,2,4triazinyl), 6-(1,2,4-triazinyl), 4-(1,2,3-triazinyl) and 5-(1,2,3-triazinyl).

Representative examples of five-membered heterocycles include 2-furyl; 3-furyl; 2-thienyl; 3-thienyl; 4-(1,2,3-triazolyl); 3-(1,2,4-triazolyl); 5-(1,2,4-triazolyl), 2-pyrrolyl; 2-oxazolyl; and the like.

The general reaction is shown in Equation I.

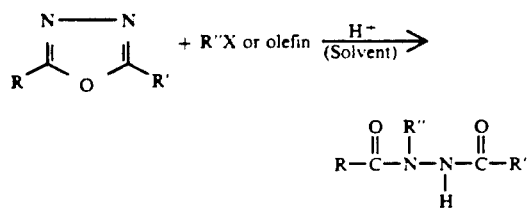

Where R and R' may be $(C_6-C_{10})$aryl, 5- or 6-membered heterocycle, $(C_1-C_{10})$alkyl, $(C_1-C_{10})$alkoxy, $(C_1-C_{10})$alkenyl, $(C_2-C_{10})$alkenoxy and amino. The aryl and heterocycle may be substituted with one to three of the same or different $(C_1-C_6)$alkyl, $(C_1-C_6)$haloalkyl, $(C_1-C_6)$alkoxy, $(C_1-C_6)$haloalkoxy, hydroxy, halo, nitro, cyano, carboxy, $(C_1-C_6)$alkoxycarbonyl, $(C_1-C_6)$alkylcarbonyl or amino. The amino may be substituted with one or two of the same or different $(C_1-C_6)$alkyl, $(C_2-C_6)$haloalkyl, cyano, carboxy, $(C_1-C_6)$alkoxycarbonyl, $(C_1-C_6)$alkylcarbonyl or amino. The alkyl, alkoxy, alkenyl and alkenoxy moieties may be substituted with one to three of the same or different $(C_1-C_6)$alkoxy, $(C_1-C_6)$haloalkoxy, hydroxy, halo, nitro, cyano, carboxy, $(C_1-C_6)$alkoxycarbonyl, $(C_1-C_6)$alkylcarbonyl or amino. Preferably, R and R' are independently substituted or unsubstituted $(C_1-C_{10})$aryl, 5- or 6-membered heterocycle or $(C_1-C_{10})$alkyl.

R" is a tertiary carbon containing alkyl and, preferably, R" is t-butyl. The olefin can, on protonation, yield a tertiary carbonium ion where the substituents are alkyl groups.

The solvent may or may not be present.

The following examples will further illustrate the invention but are not intended to limit it in any way.

EXAMPLE NO. 1

Glacial acetic acid (6 ml) and 2.25 g of 2,5-diphenyl-1,3,4-oxadiazole (10 mmol) were added to a 25 ml flask. Concentrated sulfuric acid (20 mmol) was added, then t-butanol (1.48 g, 20 mmol) was added dropwise over one-half hour. The reaction mixture was stirred at room temperature for 45 hours, then poured into dilute base and extracted with methylene chloride. The organic phase was washed with water and stripped, and the crude product was purified by flash chromatography to give 1.24 g (42% yield) of 1-t-butyl-1,2-dibenzoylhydrazide, mp 173.5–175° C.

The examples set forth in Table 1 generally followed the procedure set forth in Example No. 1.

TABLE 1

| Exam. No. | Oxadiazole | Solvent | Acid (eq) | $R_1X$ (eq) | Temp. °C. | Time | Conversion | Product |
|---|---|---|---|---|---|---|---|---|
| 2. | 2,5-diphenyl-1,3,4-oxadiazole | HOAc | $H_2SO_4$ (1) | t-BuOH (2) | 40 | 13.5 h | 20% | N'-t-butyl-N,N'-dibenzoylhydrazine |
| 3. | 2,5-diphenyl-1,3,4-oxadiazole | HOAc | $H_2SO_4$ (1) | t-BuOH (excess) | 70 | 24 h | 22% | N'-t-butyl-N,N'-dibenzoylhydrazine |
| 4. | 2,5-diphenyl-1,3,4-oxadiazole | HOAc | $H_2SO_4$ (1) | t-BuOH (1) | RT | 6.5 d | 25% | N'-t-butyl-N,N'-dibenzoylhydrazine |
| 5. | 2,5-diphenyl-1,3,4-oxadiazole | HOAc | $H_2SO_4$ (1) | t-BuOH (2) | RT | 16 h | 21% | N'-t-butyl-N,N'-dibenzoylhydrazine |
| 6. | 2,5-diphenyl-1,3,4-oxadiazole | HOAc | $H_2SO_4$ (2) | t-BuOH (1) | RT | 16 h | 54% | N'-t-butyl-N,N'-dibenzoylhydrazine |
| 7. | 2,5-diphenyl-1,3,4-oxadiazole | HOAc | $H_2SO_4$ (1) | t-BuOAc (2) | reflux | 1 h | 11% | N'-t-butyl-N,N'-dibenzoylhydrazine |
| 8. | 2,5-diphenyl-1,3,4-oxadiazole | HOAc | $H_2SO_4$ (2) | t-BuOH (4) | RT | 21 h | 44% | N'-t-butyl-N,N'-dibenzoylhydrazine |
| 9. | 2,5-diphenyl-1,3,4-oxadiazole | HOAc | $H_2SO_4$ (3) | t-BuOH (1) | RT | 45 h | 43% | N'-t-butyl-N,N'-dibenzoylhydrazine |
| 10. | 2,5-diphenyl-1,3,4-oxadiazole | HOAc | $H_2SO_4$ (1) | t-BuOAc (1) | RT | 22 h | 37% | N'-t-butyl-N,N'-dibenzoylhydrazine |
| 11. | 2,5-diphenyl-1,3,4-oxadiazole | HOAc | $H_2SO_4$ (2) | t-BuOAc (2) | RT | 5.5 h | 79% | N'-t-butyl-N,N'-dibenzoylhydrazine |
| 12. | 2,5-diphenyl-1,3,4-oxadiazole | HOAc | $H_2SO_4$ (2) | t-BuCl (1) | RT | 93 h | 2% | N'-t-butyl-N,N'-dibenzoylhydrazine |
| 13. | 2,5-diphenyl-1,3,4-oxadiazole | HOAc | $H_2SO_4$ (2) | isobutylene (excess) | RT | 96 h | 75% | N'-t-butyl-N,N'-dibenzoylhydrazine |
| 14. | 2,5-diphenyl-1,3,4-oxadiazole | HOAc | TsOH (2) | t-BuOH (2) | RT | 1 wk | 30% | N'-t-butyl-N,N'-dibenzoylhydrazine |
| 15. | 2,5-diphenyl-1,3,4-oxadiazole | None | $CF_3SO_3H$ (0.4) | t-BuOH | reflux | 4 d | 22% | N'-t-butyl-N,N'-dibenzoylhydrazine |
| 16. | 2,5-diphenyl-1,3,4-oxadiazole | None | $H_2SO_4$ (1) | t-BuOH | reflux | 2 h | 11% | N'-t-butyl-N,N'-dibenzoylhydrazine |
| 17. | 2,5-diphenyl-1,3,4-oxadiazole | $H_2O$ | $H_2SO_4$ (1) | t-BuOH (9:1 $H_2O$) | reflux | 4.5 h | 22% | N'-t-butyl-N,N'-dibenzoylhydrazine |
| 18. | 2,5-diphenyl-1,3,4-oxadiazole | diethyl ether | $H_2SO_4$ (2) | t-BuOH (2) | RT | 48 h | 5% | N'-t-butyl-N,N'-dibenzoylhydrazine |
| 19. | 2,5-diphenyl-1,3,4-oxadiazole | EtOAc | $H_2SO_4$ (2) | t-BuOH (2) | RT | 48 h | 28% | N'-t-butyl-N,N'-dibenzoylhydrazine |
| 20. | 2,5-diphenyl-1,3,4-oxadiazole | HOAc | $H_2SO_4$ (2) | 2-Methyl-2-hexanol (1) | RT | 20 h | 20% | N'-(1,1-dimethylpentyl)-N,N'-dibenzoylhydrazine |
| 21. | 2-(4-ethylphenyl)- | HOAc | $H_2SO_4$ | t-BuOH | RT | 46 h | 17% | N'-t-butyl-N'-(3,5- |

TABLE 1-continued

| Exam. No. | Oxadiazole | Solvent | Acid (eq) | R₁X (eq) | Temp. °C. | Time | Conversion | Product |
|---|---|---|---|---|---|---|---|---|
| | 5-(3,5-dimethyl-phenyl)-1,3,4-oxadiazole | | (2) | (2) | | | 14% | dimethylbenzoyl)-N-(4-ethylbenzoyl)hydrazine; N-t-butyl-N'-(3,5-dimethyl-benzoyl)-N-(4-ethyl-benzoyl)-hydrazine |
| 22. | 2-methyl-5-phenyl-1,3,4-oxadiazole | HOAc | H₂SO₄ (2) | t-BuOH (2) | RT | 72 h | 55% | N'-t-butyl-N'-methyl carbonyl-N-benzoyl-hydrazine; |
| | | | | | | | 14% | N-t-butyl-N'-methylcarbonyl-N-benzoylhydrazine |
| 23. | 2-furyl-5-phenyl-1,3,4-oxadiazole | HOAc | H₂SO₄ (2) | t-BuOH (2) | RT | 24 h | 55% | N'-t-butyl-N'-furoyl-N-benzoylhydrazine; |
| | | | | | | | 4% | N'-t-butyl-N-furoyl-N'-benzoylhyrazine |
| 24. | 2-phenyl-1,3,4-oxadiazole | HOAc | H₂SO₄ (2) | t-BuOH (2) | RT | 72 h | 42% | N'-t-butyl-N-benzoyl-N'-formylhydrazine |
| 25. | 2,5-diphenyl-1,3,4-oxadiazole | EtOAc | H₂SO₄ (2) | t-BuOAc (2) | 0 | 7.25 h | 2% | N'-t-butyl-N,N'-dibenzoylhydrazine |
| 26. | 2,5-diphenyl-1,3,4-oxadiazole | HOAc | H₂SO₄ (2) | 2,3-dimethyl-2-butene (2) | RT | 1 wk | 8% | N'-(2,3-dimethyl-2-butyl)-N,N'-dibenzoyl-hydrazine |
| 27. | 2,5-diphenyl-1,3,4-oxadiazole | HOAc | H₂SO₄ (2) | di-t-butyl dicarbonate (2) | RT | 5 h | 54% | N'-t-butyl-N,N'-dibenzoylhydrazine | eq means equivalents
d means days
h means hours
wk means week
R₁X is a tertiary carbon cation precursor
HOAc is glacial acetic acid
H₂SO₄ is sulfuric acid
t-BuOH is tertiary butanol
t-BuOAc is tertiary butyl acetate
t-BuCl is tertiary butyl chloride
RT is room temperature
TsOH is p-toluenesulfonic acid
CF₃SO₃H is trifluoromethane sulfonic acid
EtOAc is ethyl acetate No alkylated dibenzoylhydrazine was observed under the conditions tested with isopropanol, benzyl alcohol, α, α-dimethylbenzyl alcohol, acetone cyanohydrin, 2,2-dimethoxypropane, benzylacetate or diisobutylene.

It should be understood that the instant specification and examples are set forth by way of illustration and not limitation, and that various modifications and changes may be made without departing from the spirit and scope of the present invention as defined by the appended claims.

I claim:

1. A process for preparing a N-t-alkyl-1,2-diacylhydrazine comprising reacting a 1,3,4-oxadiazole with a tertiary alkyl cation precursor in the presence of a strong acid catalyst;said acid catalyst being substantially free of the corresponding acid anhydride.

2. The process of claim 1 wherein the 1,3,4-oxadiazole is a 2,5-disubstituted-1,3,4-oxadiazole.

3. The process of claim 2 wherein the 1,3,4-oxadiazole substituents are independently selected from the group consisting of $(C_6-C_{10})$aryl, 5- or 6-membered heterocycle, $(C_1-C_{10})$alkyl, $(C_1-C_{10})$alkoxy, $(C_2-C_{10})$alkenyl, $(C_2-C_{10})$alkenoxy and amino, where the aryl and heterocycle may be substituted with one to three of the same or different $(C_1-C_6)$alkyl, $(C_1-C_6)$haloalkyl, $(C_1-C_6)$alkoxy, $(C_1-C_6)$haloalkoxy, hydroxy, halo, nitro, cyano, carboxy, $(C_1-C_6)$alkoxycarbonyl, $(C_1-C_6)$alkylcarbonyl or amino, where the amino may be substituted with one or two of the same or different $(C_1-C_6)$alkyl, $(C_2-C_6)$haloalkyl, cyano, carboxy, $(C_1-C_6)$alkoxycarbonyl, $(C_1-C_6)$alkylcarbonyl or amino and where the alkyl, alkoxy, alkenyl and alkenoxy may be substituted with one to three of the same or different $(C_1-C_6)$alkoxy, $(C_1-C_6)$haloalkoxy, hydroxy, halo, nitro, cyano, carboxy, $(C_1-C_6)$alkoxycarbonyl, $(C_1-C_6)$alkylcarbonyl or amino.

4. The process of claim 3 wherein the 1,3,4-oxadiazole substituents are independently substituted or unsubstituted $(C_6-C_{10})$aryl, 5- or 6-membered heterocycle or $(C_1-C_{10})$alkyl.

5. The process of claim 4 wherein at least one of the 1,3,4-oxadiazole substituents is a substituted or unsubstituted phenyl.

6. The process of claim 5 wherein the 1,3,4-oxadiazole substituents are both independently substituted or unsubstituted phenyl.

7. The process of claim 1 wherein the tertiary alkyl cation precursor is selected from the group consisting of an alcohol, ester, ether, carbonate, halogen or olefin.

8. The process of claim 7 wherein the tertiary alkyl cation precursor is selected from the group consisting of an alcohol, acetate, benzoate, methyl ether, ethyl ether, carbonate, chloride, bromide or olefin.

9. The process of claim 8 wherein the tertiary alkyl cation precursor is selected from the group consisting of t-butanol, t-butyl acetate, t-butyl benzoate, t-butylmethyl ether, t-butylethyl ether, di-t-butyldicarbonate, t-butylchloride, t-butylbromide and isobutylene.

10. The process of claim 7 wherein the tertiary alkyl cation precursor has the formula

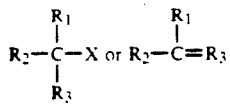

where $R_1$, $R_2$ and $R_3$ are independently ($C_1$-$C_6$)alkyl, ($C_2$-$C_6$)alkenyl or ($C_2$-$C_6$)alkynyl and X is OH, OOCCH$_3$, OOCC$_6$H$_5$, OCH$_3$, OCH$_2$CH$_3$, Cl or Br.

11. The process of claim 1 wherein the strong acid catalyst is a sulfur containing acid.

12. The process of claim 11 wherein the strong acid catalyst is selected from the group consisting of sulfuric acid, p-toluenesulfonic acid monohydrate, trifluoromethanesulfonic acid and methanesulfonic acid.

13. The process of claim 12 wherein the strong acid catalyst is sulfuric acid.

14. The process of claim 1 wherein the reactants are reacted in the presence of a solvent.

15. The process of claim 14 wherein the solvent is selected from the group consisting of low molecular weight acids, esters, alcohols and ethers other than the strong acid catalyst.

16. The process of claim 15 wherein the solvent is acetic acid, ethyl acetate, methyl benzoate or diethyl ether.

17. The process of claim 16 wherein the solvent is acetic acid.

18. The process of claim 1 wherein the reaction is carried out between −20° C. and 98° C.

19. The process of claim 18 wherein the reaction is carried out between 0° C. and 98° C.

20. The process of claim 19 wherein the reaction is carried out between 15° C. and 60° C.

21. The process of claim 20 wherein the reaction is carried out between 20° C. and 30° C.

22. The process of claim 1 comprising reacting a 2,5-diaryl-1,3,4-oxadiazole with t-butanol, t-butyl acetate, t-butyl chloride or isobutylene in the presence of sulfuric acid and acetic acid at a temperature of between 15° C. and 60° C.

23. The process of claim 22 wherein the aryl substituents of the 1,3,4-oxadiazole are independently phenyl or phenyl substituted with one to three of the same or different halo, ($C_1$-$C_6$)alkyl, ($C_1$-$C_6$)haloalkyl, hydroxy or ($C_1$-$C_6$)alkoxy.

* * * * *

UNITED STATES PATENT AND TRADEMARK OFFICE
CERTIFICATE OF CORRECTION

PATENT NO.  : 5,110,986
DATED       : May 5, 1992
INVENTOR(S) : Martha J. Kelly

It is certified that error appears in the above-identified patent and that said Letters Patent is hereby corrected as shown below:

Col. 1, l. 65: replace "halogen" with --haloalkyl--

Col. 2, l. 46: insert "u" between "l" and "o" of trifloromethoxy

Col. 3, l. 9: insert "-" between "4" and "t" of 5-(1,2,4-triazinyl)

Col. 4, l. 3: delete "subscript '-' " between "$C_{-6}$)" of $(C_1-C_{-6})$ alkoxycarbonyl Col. 4, l. 9: change "$(C_1-C_{1-}$" to -- $(C_1-C_{10})_-$ --

Col. 4, l. 30: change "zide" to "zine"

Col. 5, l. 58-59: change "$(C_2-C1-0)$alkenyl to -- $(C_2-C_{10})$ alkenyl--.

Col. 6, l. 57: replace "halogen" with --haloalkyl--

Signed and Sealed this

Ninth Day of November, 1993

Attest:

BRUCE LEHMAN

*Attesting Officer*    *Commissioner of Patents and Trademarks*